(12) United States Patent
Petill et al.

(10) Patent No.: US 11,543,242 B2
(45) Date of Patent: Jan. 3, 2023

(54) LOCALIZATION AND VISUALIZATION OF SOUND

(71) Applicant: MICROSOFT TECHNOLOGY LICENSING, LLC, Redmond, WA (US)

(72) Inventors: Scott David Petill, Seattle, WA (US); Oscar E. Murillo, Redmond, WA (US); Rebecca Sundling Haruyama, Bellevue, WA (US); Melissa Hellmund Vega, Vancouver (CA)

(73) Assignee: Microsoft Technology Licensing, LLC, Redmond, WA (US)

( * ) Notice: Subject to any disclaimer, the term of this patent is extended or adjusted under 35 U.S.C. 154(b) by 235 days.

(21) Appl. No.: 16/879,598

(22) Filed: May 20, 2020

(65) Prior Publication Data
US 2021/0364281 A1 Nov. 25, 2021

(51) Int. Cl.
*G01B 17/00* (2006.01)
*G10L 25/51* (2013.01)
(Continued)

(52) U.S. Cl.
CPC ......... *G01B 17/00* (2013.01); *G02B 27/0172* (2013.01); *G06T 19/006* (2013.01); *G10L 25/51* (2013.01); *G02B 2027/0178* (2013.01)

(58) Field of Classification Search
CPC .............. G01B 17/00; G02B 27/0172; G02B 2027/0178; G06T 19/006; G10L 25/51;
(Continued)

(56) References Cited

U.S. PATENT DOCUMENTS

| 7,113,610 B1 | 9/2006 | Chrysanthakopoulos |
| 9,280,914 B2 | 3/2016 | Wang et al. |

(Continued)

FOREIGN PATENT DOCUMENTS

| CN | 110673819 A | 1/2020 |
| CN | 111128180 A | 5/2020 |

(Continued)

OTHER PUBLICATIONS

Jain, et al., "Head-Mounted Display Visualizations to Support Sound Awareness for the Deaf and Hard of Hearing", In Proceedings of the 33rd Annual ACM Conference on Human Factors in Computing Systems, Apr. 18, 2015, 10 Pages.
(Continued)

*Primary Examiner* — Andrew Sasinowski
(74) *Attorney, Agent, or Firm* — NovoTechIP International PLLC

(57) ABSTRACT

A method of and system for visualizing a sound source is disclosed. The method may include analyzing an audio signal received by a sound transducer to determine a positional direction of the sound source, determining whether the positional direction of the sound source falls outside a field of view of a user, and in response to determining that the positional direction of the sound source falls outside the field of view of the user, rendering on a display unit a visual representation of the sound source. The visual representation of the source is rendered on a virtual surface at a location within the field of view of the user, the location corresponding to at least one of a distance of the source from the user and a positional direction of the source with respect to the user.

17 Claims, 10 Drawing Sheets

(51) Int. Cl.
*G02B 27/01* (2006.01)
*G06T 19/00* (2011.01)

(58) Field of Classification Search
CPC .............. H04R 2499/15; H04R 3/005; H04R 2430/20; G06F 3/012; G06F 3/167; A61F 4/00
See application file for complete search history.

(56) References Cited

U.S. PATENT DOCUMENTS

| | | | |
|---|---|---|---|
| 9,560,446 B1* | 1/2017 | Chang | H04R 1/406 |
| 10,111,013 B2 | 10/2018 | Hu | |
| 10,353,198 B2 | 7/2019 | Sakai | |
| 2016/0080874 A1* | 3/2016 | Fullam | G06F 3/165 |
| | | | 381/313 |
| 2016/0188291 A1* | 6/2016 | Vilermo | H04M 1/72454 |
| | | | 345/156 |
| 2017/0123492 A1* | 5/2017 | Marggraff | G06F 3/04845 |
| 2018/0061136 A1 | 3/2018 | Lehtiniemi et al. | |
| 2020/0082842 A1* | 3/2020 | Brown | G06F 3/167 |

FOREIGN PATENT DOCUMENTS

| | | |
|---|---|---|
| ES | 2245203 A1 | 12/2005 |
| JP | 2015212667 A | 11/2015 |
| WO | 2020079485 A2 | 4/2020 |

OTHER PUBLICATIONS

"International Search Report and Written Opinion Issued in PCT Application No. PCT/US21/028052", dated Aug. 4, 2021, 12 Pages.

* cited by examiner

LOCALIZATION AND VISUALIZATION OF SOUND

BACKGROUND

A large number of people in the world suffer from mild to severe hearing impairment. Often people with hearing impairment rely on other senses such as vision to interpret their environment. As a result, it may be particularly challenging for people who suffer from hearing impairment to notice events that occur outside of their field of view. This may also be true for people with normal hearing that work in noisy environments, particularly if they are focusing on a task that requires their full attention. People that utilize devices that provide virtual reality (VR), augmented reality (AR), and/or mixed reality (MR) may also have trouble paying attention to events that occur outside their field of view as the environments generated by these devices may consume all their attention (e.g., an immersive environment). This may result in the user being unaware of important and/or dangerous sounds that originate from outside their field of view.

Hence, there is a need for improved methods and system of notifying people with hearing challenges of sounds that originate from outside the person's field of view.

SUMMARY

In one general aspect, the instant disclosure presents an electronic device having a sound transducer for receiving an audio signal, a display unit, a processing unit, and a memory readable by the processing unit and comprising instructions stored thereon to cause the processing unit to perform multiple functions. The function may include analyze an audio signal received by the sound transducer to determine a positional direction of a source of the received audio signal, determine whether the positional direction of the source falls outside a field of view of a user of the electronic device, and in response to determining that the positional direction of the source falls outside the field of view of the user of the electronic device, render on the display unit a visual representation of the source. In some implementations, the visual representation of the source is rendered on a virtual surface at a location within the field of view of the user, the location corresponding to at least one of a distance of the source from the user and a positional direction of the source with respect to the user.

In yet another general aspect, the instant application describes a method for visualizing a sound source. The method may include analyzing an audio signal received by a sound transducer to determine a positional direction of the sound source, determining whether the positional direction of the sound source falls outside a field of view of a user, and in response to determining that the positional direction of the sound source falls outside the field of view of the user, rendering on a display unit a visual representation of the sound source, wherein the visual representation of the sound source is rendered on a virtual surface at a location within the field of view of the user, the location corresponding to at least one of a distance of the sound source from the user and a positional direction of the sound source with respect to the user.

In a further general aspect, the instant application describes a non-transitory computer readable medium on which are stored instructions that when executed cause a programmable device to analyze an audio signal received by a sound transducer to determine a positional direction of a sound source of the received audio signal, determine whether the positional direction of the sound source falls outside a field of view of a user, and in response to determining that the positional direction of the sound source falls outside the field of view of the user, rend on a display unit a visual representation of the sound source, wherein the visual representation of the source is rendered on a virtual surface at a location within the field of view of the user, the location corresponding to at least one of a distance of the source from the user and a positional direction of the source with respect to the user.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The drawing figures depict one or more implementations in accord with the present teachings, by way of example only, not by way of limitation. In the figures, like reference numerals refer to the same or similar elements. Furthermore, it should be understood that the drawings are not necessarily to scale.

DETAILED DESCRIPTION

Figure 1:
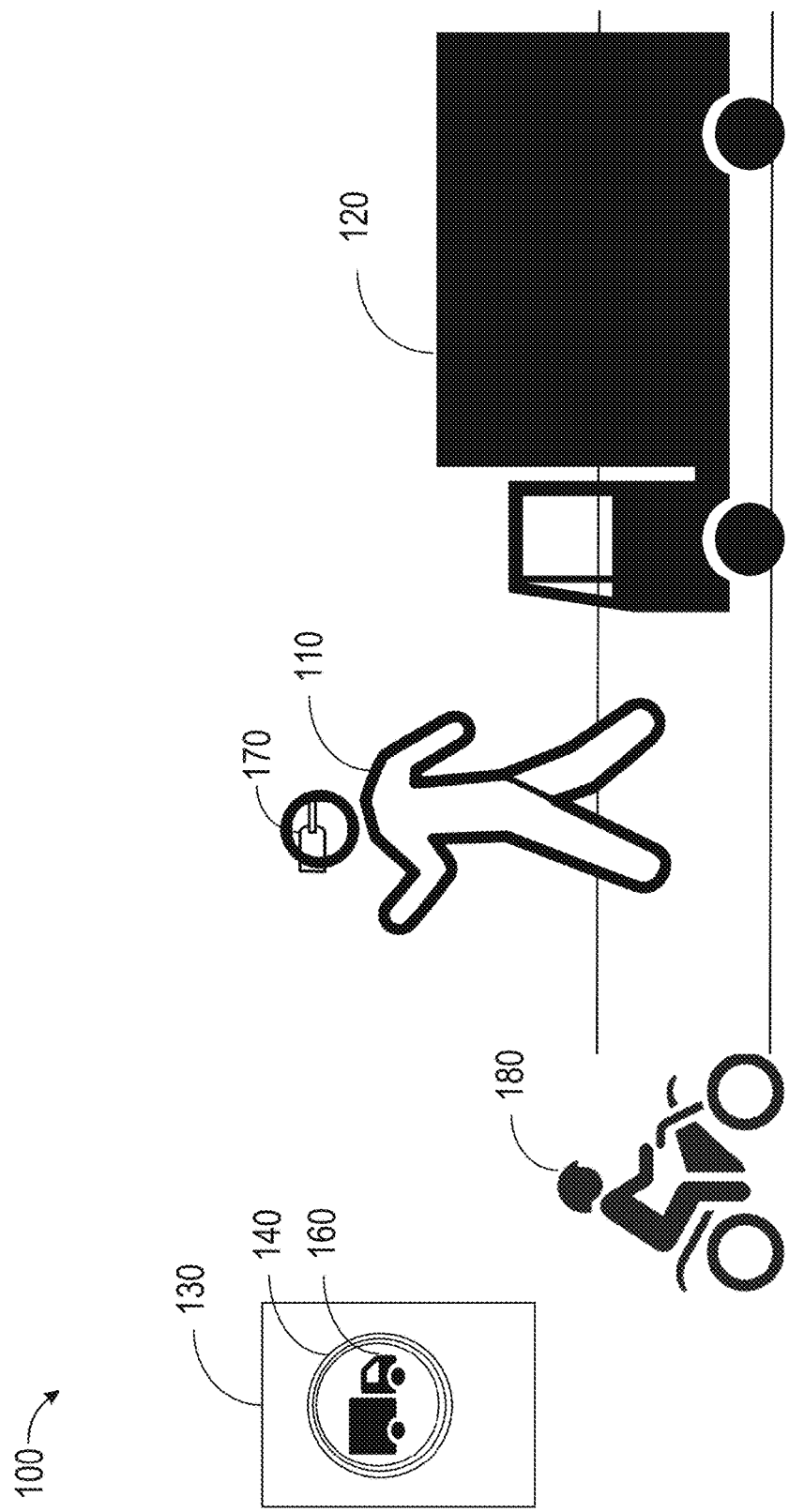
FIG. 1 depicts a block diagram of an example environment upon which aspects of this disclosure may be implemented.

In the following detailed description, numerous specific details are set forth by way of examples in order to provide a thorough understanding of the relevant teachings. It will be apparent to persons of ordinary skill, upon reading this description, that various aspects can be practiced without such details. In other instances, well known methods, procedures, components, and/or circuitry have been described at a relatively high-level, without detail, in order to avoid unnecessarily obscuring aspects of the present teachings.

Some degree of hearing impairment is prevalent in a percentage of the world's population. People with hearing impairment can often recognize sources of sound in their environment if they can see them. However, if the source of the sound is outside the person's field of view, it may be difficult for the person to perceive it. The same may apply to people with normal hearing who are utilizing a noise cancelling device, a head-mounted display device, and/or who are present in noisy environments. This may be result in the person not realizing that important and/or dangerous events are occurring in their environment. For example, a person working in a noisy construction site wearing a helmet may not hear a forklift that is quickly approaching from behind. Similarly, a person of hearing impairment may not notice a crying baby, if the baby is located behind them.

Some existing hearing aid devices include mechanisms for identifying sound sources and generating visualizations that correspond to the identified sound sources. However, these mechanisms do not differentiate between sound sources that originate from outside the person's field of view and those that do not. As a result, such devices may generate visualizations for all sound sources that they perceive. The result may be a crowded display of multiple visualizations on the same screen. This may be particularly true in noisy environments where there are several sources of sound. Such crowded visualizations may be confusing and overwhelming for the user to view and decipher. Furthermore, the visualization may not help the user quickly identify important and/or dangerous sources of sound that are located outside their field of view (e.g., behind them). Still further, processing and visualizing sources of sound from the user's surrounding, including those that originate from within the user's field of view may require significant processing and memory resources.

To address these technical problems and more, in an example, this description provides a technical solution for a method of identifying, localizing and visualizing sound sources that are outside a user's field of view. To improve the current methods of localization and visualization of sound sources, the technical solution provides a method of identifying sound sources that originate from outside the user's field of view, determining location of the sound sources with respect to the user and visualizing the sound sources in a manner that reveals to the user that the sound source originates from outside the user's field of view. In some implementations, sound signals are analyzed to identify their source and/or their intensity and to determine whether the sound source should be visualized based at least in part on the identity of the sound source and/or the intensity. The visualization may be provided by a visual representation of the sound on a virtual surface at a location that corresponds with the location of the source. Thus, the technical solution offers an efficient mechanism for identifying important sound sources that originate from outside the user's field of view and visualizing them in a manner that brings those sound sources to the user's attention effectively.

As will be understood by persons of skill in the art upon reading this disclosure, benefits and advantages provided by such technical solutions can include, but are not limited to, a solution to the technical problems of ineffective and resource intensive visualization and localization of sound sources for users who have difficulty noticing a sound that originates from outside their field of view. Technical solutions and implementations provided herein optimize and improve the process of identifying, localizing and visualizing sound sources that originate from outside the user's field of view. Thus, the benefits provided by these technical solutions include providing increased efficiency, accuracy and effectiveness in bringing the user's attention to important and/or dangerous sounds that originate from outside their field of view. Furthermore, in some implementations, because only sound sources that originate from outside the user's field of view are processed, computing resources may be conserved.

As a general matter, the methods and systems described here may include, or otherwise make use of, a machine-trained model to provide translations. Machine learning (ML) generally includes various algorithms that a computer automatically builds and improves over time. The foundation of these algorithms is generally built on mathematics and statistics that can be employed to predict events, classify entities, diagnose problems, and model function approximations. As an example, a system can be trained using data generated by an ML model in order to identify sound sources and determine associations between sound sources, sound intensity, location and danger and/or importance of the sound source. Such training may be made following the accumulation, review, and/or analysis of user data from a large number of users over time. Such user data is configured to provide the ML algorithm (MLA) with an initial or ongoing training set. In addition, in some implementations, a user device can be configured to transmit data captured locally during use of relevant application(s) to a local or remote ML algorithm and provide supplemental training data that can serve to fine-tune or increase the effectiveness of the MLA. The supplemental data can also be used to improve the training set for future application versions or updates to the current application.

In different implementations, a training system may be used that includes an initial ML model (which may be referred to as an "ML model trainer") configured to generate a subsequent trained ML model from training data obtained from a training data repository or from device-generated data. The generation of both the initial and subsequent trained ML model may be referred to as "training" or "learning." The training system may include and/or have access to substantial computation resources for training, such as a cloud, including many computer server systems adapted for machine learning training. In some implementations, the ML model trainer is configured to automatically generate multiple different ML models from the same or similar training data for comparison. For example, different underlying MLAs, such as, but not limited to, decision trees, random decision forests, neural networks, deep learning (for example, convolutional neural networks), support vector machines, regression (for example, support vector regression, Bayesian linear regression, or Gaussian process regression) may be trained. As another example, size or complexity of a model may be varied between different ML models, such as a maximum depth for decision trees, or a number and/or size of hidden layers in a convolutional neural network. As another example, different training approaches may be used for training different ML models, such as, but not limited to, selection of training, validation, and test sets of training data, ordering and/or weighting of training data items, or numbers of training iterations. One or more of the resulting multiple trained ML models may be selected based on factors such as, but not limited to, accuracy, computational efficiency, and/or power efficiency. In some implementations, a single trained ML model may be produced.

The training data may be continually updated, and one or more of the ML models used by the system can be revised or regenerated to reflect the updates to the training data. Over time, the training system (whether stored remotely, locally, or both) can be configured to receive and accumulate more training data items, thereby increasing the amount and variety of training data available for ML model training, resulting in increased accuracy, effectiveness, and robustness of trained ML models.

FIG. 1 illustrates an example environment 100, upon which aspects of this disclosure may be implemented. The environment 100 may include a user 110 wearing a head-mounted display (HMD) device 170. The user 110 may be a person who suffers from hearing impairment and/or a person who is presently in a noisy environment (e.g., a noisy work environment). In some implementations, the user 110 may simply be a user wearing the HMD 170. In an example, the HDM device 170 generates an immersive environment. An immersive environment may refer to virtual reality (VR), augmented reality (AR), and/or mixed reality (MR) environments. The HMD device 170 may display one or more virtual objects within the immersive environment which, in one implementation, interact with the user 110. The virtual objects may include one or more holograms that are movable within the immersive environment.

Whether it is because of hearing impairment, high noise level and/or distraction caused by the immersive environment, the user 110 may have difficulty hearing certain sounds from the ambient environment. However, because the user can still see sources of sound that are within the user's field of view, the user is likely to be aware of those sources. For example, if the user 110 cannot hear the motorcycle 180, the user 110 is still likely to be aware of its existence because the user 110 can see the motorcycle 180. As a result, the user 110 can react in time to avoid a potential accident. That may not be true for the sound source 120. Because the sound source 120 is located outside the user's field of view (e.g., behind the user 110), if the user 110 cannot hear the sound source 120 approaching (e.g., cannot hear the truck honking), the user 110 is unlikely to be aware of the sound source 120. This can be dangerous, particularly in fast-pasted crowded environments such as a factory floor or a construction site.

To make the user 110 aware of important and dangerous sound sources that are outside the user's field of view, the HDM device 170 may generate a visual representation 160 of such sound sources. This may involve identifying sound sources that are significant to the user 110 (e.g., a crying baby, a coworker speaking right behind the user, a door opening or closing, or the sound of the user's telephone ringing) and/or sound sources that indicate a level of risk to the user 110 (e.g., a moving vehicle approaching from behind the user, sounds of falling debris, or alerts from a machinery). Such sound sources may be referred to herein as important sound sources. The process of identifying important sound sources is discussed in detail below with respect to FIG. 3. Once important sound sources that are outside the user's field of view are identified, the visual representation 160 of the sound source may be generated by the HDM device 170 and displayed at a virtual surface such as the virtual surface 130.

The virtual surface 130 may be displayed at a location in front of the user that corresponds with the location of the sound source 120 behind the user. For example, the virtual surface 130 may be displayed at a location where the distance from the visual representation 160 to the user is proportional to the distance from the sound source 120 to the user. In an example, this is done by displaying the visual representation 160 on the HDM device 170 such that the visual representation 160 appears to be the same distance away from the user 110 as the sound source 120 (e.g., when the sound source 120 is 15 feet away behind the user 110, the visual representation 160 appears to be 15 feet in front of the user). This may be done to such that the visual representation 160 provides an approximation to the user 110 of location of the sound source 120 behind the user. In some implementations, the visual representation 160 is rendered on the virtual surface 130 at a location that corresponds to a reflector location of the sound source 120 location. In this manner, the virtual surface 130 may operate in a similar manner as a rearview mirror by displaying sound sources that originate from behind the user 110 on a reflective virtual surface. Thus, sound sources that are located on the right side behind the user 110 may be displayed on the virtual surface 130 on the right side of the virtual surface 130. Similarly, sound sources that are located on the left side behind the user 110 may be displayed on the virtual surface 130 on the left side of the virtual surface 130.

In some implementations, the visual representation 160 is a holographic object that corresponds to the shape of the sound source. For example, when the sound source 120 is a truck, a truck hologram may be used to display the visual representation 160. Furthermore, certain virtual objects such as virtual objects 140 may be used to represent sound intensity (e.g. loudness). In some implementations, the virtual objects 140 include circles drawn around the visual representation 160. In an example, the number of the circles represents the intensity of the sound. For example, the louder the sound, the more circles may be drawn around the visual representation 160. In alternative implementations, a color is utilized to represent sound intensity. For example, a red circle may indicate that the sound is very loud, while a yellow circle may represent that the sound is moderately loud. In some implementations, the number of circles and/or the colors may change as the sound source 120 moves with respect to the user 110. For example, if the sound source 120 is getting closer to the user 110 (in which case, the intensity of the sound may also increase), the number of circles in the virtual objects 140 may be increased and/or the color may change to notify the user of the increasing danger.

It should be noted that although FIG. 1 illustrates the HMD device 170 as the device that generates the visual representation 160, other alternatives are also contemplated. For example, in one implementation, virtual representations are generated and displayed by a projector. In such a configuration, one or more devices (e.g., a gaming console and/or other devices which include one or more microphones and/or one or more cameras) that measure the environment may be used to identify sound sources located outside the user's field of view. Once such sound sources are identified, a projector may be utilized to display the visual representation of the sound sources. Other configurations are also possible. For example, in one implementation, a surround speaker system is used along with a projector and a device having a microphone (such as a mobile telephone) to communicate with a cloud-based processor to identify sound sources that are located outside the user's field of view and to display visual representation of such sounds sources on a surface that the user can view. In another example, devices that measure the environment (e.g., devices that include microphone(s) and camera(s)) may be utilized along with an HMD device to provide identification, localization and visualization of important sound sources.

Figure 2:
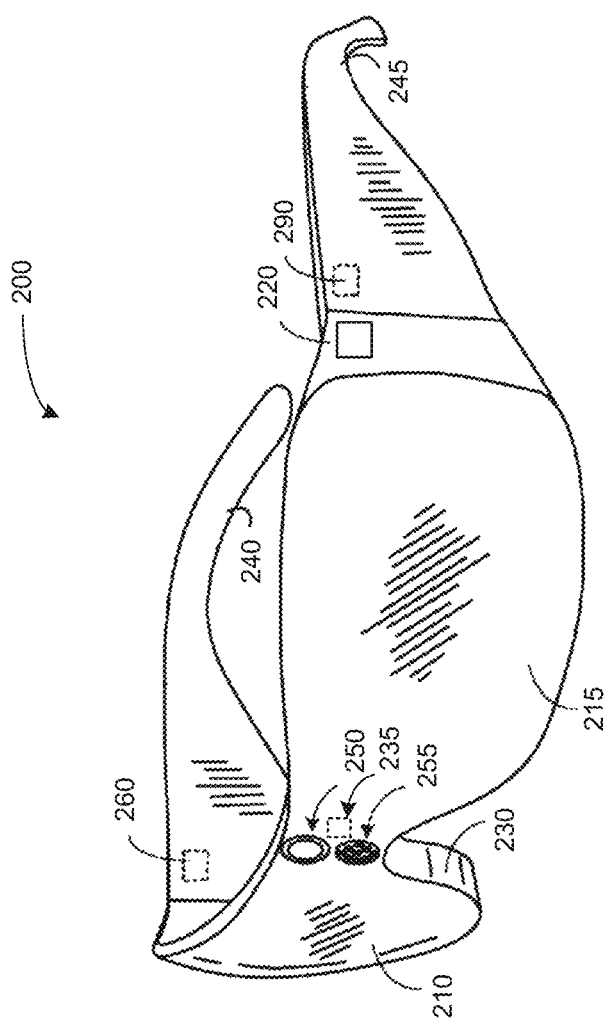
FIG. 2 depicts a diagram of an example head-mounted display device upon which aspects of this disclosure may be implemented.

FIG. 2 illustrates an example HMD device 200 which can be utilized to identify, localize and visualize important sound sources, in accordance with one or more aspects of this disclosure. In one implementation, the HMD 200 is a wearable, head-mounted augmented reality, virtual reality, or mixed-reality device that is worn by a user such as the user 110 of FIG. 1. In the illustrated example, the HMD 200 takes the form of eyeglasses and includes a nose rest 230 and left and right ear rests 240 and 245. In other examples, the HMD 200 may include a wrap-around supporting element that wraps around the user's head. In some implementations, the display device takes the form of a helmet, hat, or a wearable device visor with an in-front-of-the-face see-through visor.

In at least some implantations, the HMD device 200 includes a right display panel 210 for viewing by the user's right eye and a left display panel 215 for viewing by the user's left eye. Thus, the right display panel 210 is configured to display virtual objects at right-eye display coordinates, while the left display panel 215 is configured to display virtual objects at left-eye display coordinates. Alternatively, a single display panel can be used that extends over both the right and left eyes of the user, providing a common display that is shared by both eyes. In one implementation, the display panels 210 and 215 are at least partially transparent so the user can view the physical space of the real-world environment through the display panels. In such a configuration, the user can view virtual objects along with physical objects within the real-world environment. This creates an appearance that the virtual objects are physically present within the physical space. In this manner, the HMD device 200 can create an illusion that virtual objects move within the physical space.

In one embodiment, the HMD device 200 includes, among other features, a right-side microphone 260, a left side microphone 290 and a central microphone 235 to receive audio input from the ambient environment. The three microphones are positioned on the ear rests (on two opposing sides of the head-mounted display device 200) and the display panel to provide spatial-diversity on the HMD 200. The three microphones may enable triangulation of sound when audio signals are received at the three microphones for determining the location of the sound. In some implementations, the HMD device 200 includes an array of microphones on each of the left and right ear rests 240 and 245 to localize the sound sources. In implementations where the HMD 200 includes a wrap-around supporting element, the array of microphones may be positioned on the wrap-around supporting element. In some implementations, one or more of the microphones include a sound transducer.

In at least some implementations, the HMD device 200 also includes a variety of on-board sensors for measuring the real-world environment. These sensors include a forward-facing camera 250 for observing the physical space and a rearward-facing camera 255 for tracking the user's eye movements. The HMD 200 may include one or more additional sensors 220, which in one implementation, is an accelerometer configured to identify orientation, motion or acceleration of the HMD device 200. In some implementations, the HDM device 200 also includes one or more cameras located on the left and/or right ear rests 245 and 240, or on the back of the wrap-around supporting element when one is used. These cameras may be help identify sound sources and/or determine the positional direction and distance of the sound sources from the user when the sound source is located behind the user. Thus, by using microphones and sensors, the HMD device 200 can continuously measure and receive input from the ambient environment and the user. Additionally, the display panels 210 and 215 may enable the HMD device 200 to respond to real-world sounds and inputs by adjusting the visual representations and virtual objects displayed. In some implementations, the HDM device 200 may include additional components such as a system-on-a-chip (SoC) device/circuit, storage medium, battery, on/off button and/or transceiver.

Figure 3:
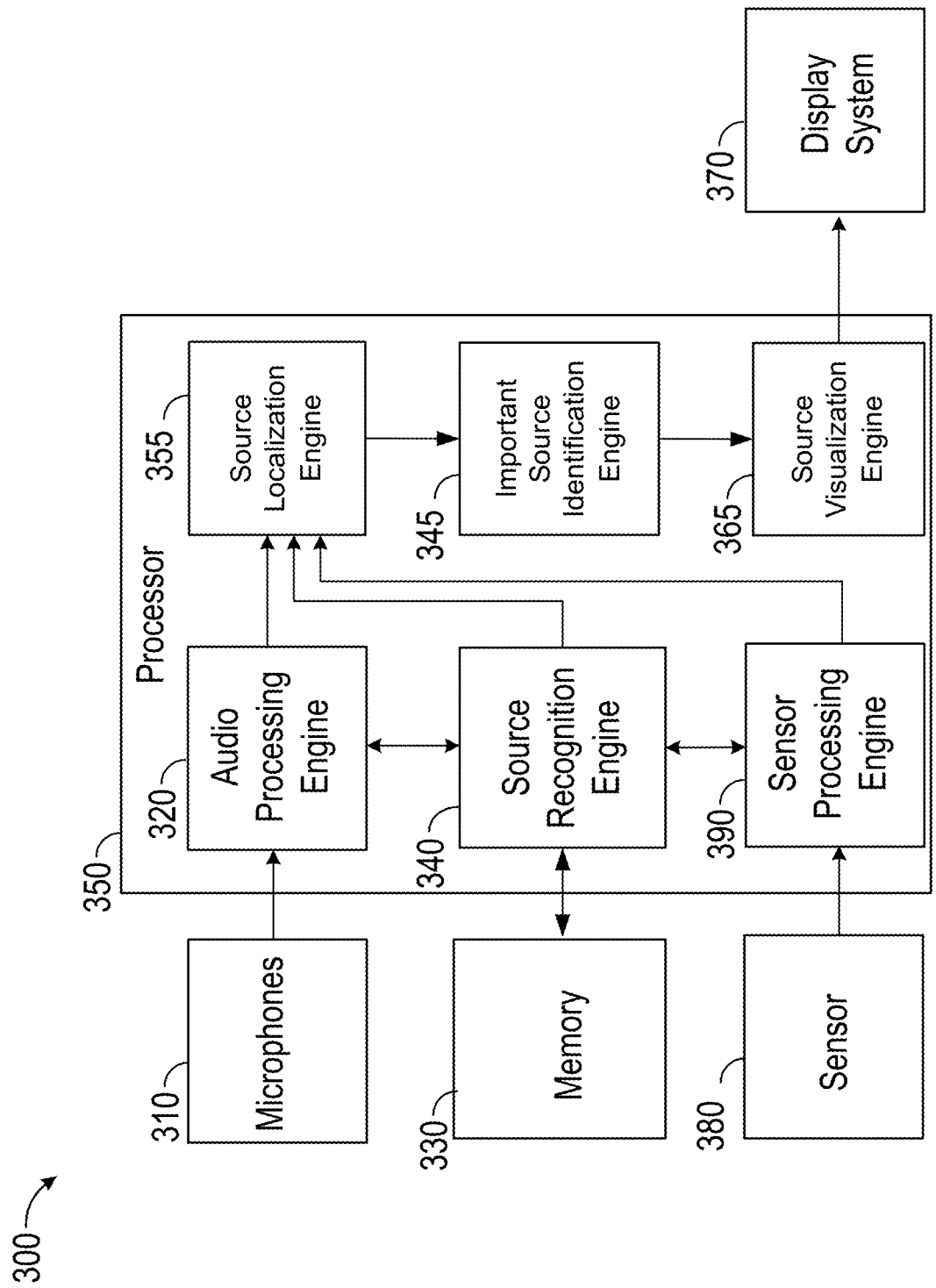
FIG. 3 depicts a diagram of a system configured to provide sound localization and visualization.

FIG. 3 illustrates an example block diagram for a system 300 providing identification, localization and visualization of important sound sources. In one implementation, the system 300 may be incorporated into an HMD device such as the HMD device 200 of FIG. 2. The system 300 may include a plurality of microphones 310. The microphones 310 may enable the system 300 to continuously listen for environmental sounds and capture audio signals from the environment when there is ambient sound in the vicinity of the system 300. The microphones 310 may be located at different locations around the environment to provide spatial diversity. In one such implementation, the microphones are arranged in a layout and used to capture sounds from various directions including locations that are outside the user's field of view. For an HMD device, this may include sounds that originate from behind the user (e.g., from the back of the HMD device). In some implementations, the layout may be designed with capturing sounds that originate from outside the field of view of the user in mind. The layout of the microphones may be predetermined. In at least one implementation, the layout is movable (e.g., when microphones are positioned around a room and are used along with a projector and/or an HMD device).

Ambient sounds may be captured as analog signals by the microphones 310 and may be digitized through the use of an analog-to-digital converter (not shown). The analog-to-digital converter may be included in one or more of the microphones 130. In some implementations, the analog-to-digital converter may be included as part of a processor 350. Once converted to digital, the audio signals may be transmitted by the microphones 310 to an audio processing engine 320.

In one implementation, the audio processing engine 320 analyzes the received audio signals to identify one or more parameters for the signals. These parameters may include volume, resolution, pitch, bandwidth, noise level, frequency, echo level, and/or ambient noise level. The ambient noise level may refer to the level of background noise in the environment, while the noise level may refer to the level of sounds in the room with a higher volume than that of the background noise. For example, when multiple people are present in a room and talking, the ambient noise is the constant murmur of voices in the room, whereas the noise level may be a phone ringing in the room.

The audio processing engine 320 may transmit the identified parameters to a source recognition engine 340 which may analyze the parameters of the audio signals to identify the source from which the sound originated. For example, the source recognition engine 340 may apply audio and voice recognition techniques to detect a particular sound. This may be performed by analyzing certain identified parameters of the received audio signals and comparing those to previously stored parameters in a memory 330 of the system 300, which is in communication with the source recognition engine 340. When some parameters such as frequency, bandwidth, resolution and the like of the received audio signal correspond with a known sound source, the source may be identified as the source of the received audio signal.

In some implementations, the source recognition engine 340 may include one or more ML models for identifying the sound source. The ML model(s) may be trained using labeled audio signal training data. The trained ML model(s) may receive the identified parameters of the received audio signal as an input and provide an identified sound source as an output. When the identified parameters do not correspond with a recognized sound source, the ML model(s) may provide an indication that the sound source is unrecognizable.

In addition to parameters of the sound signals, the source recognition engine 340 may also receive and take into account signals captured by one or more sensors 380. The sensors 380 may include sensors for capturing video, image, motion, orientation, position, acceleration, and other data about the environment and/or the user's interaction with the environment. The sensors 380 may include one or more cameras, accelerometers, motion sensors, and the like. In some implementations, the sensors 380 are positioned in a predetermined layout and used to capture signals from various points within the environment. This may be done to help the system 300 continuously capture information about the real-world environment surrounding the user.

After being captured, signals from the one or more sensors 380 may be transmitted to a sensor processing engine 390. In some implementations, the sensor processing engine 390 processes video, image, motion and/or accelerometer data to assist in identifying objects (e.g., sound sources), and in detecting and tracking the location and orientation of objects in relation to the user. In at least one implementation, the sensor processing engine 390 executes image and audio processing algorithms such as object recognition and facial recognition techniques to identify objects and people in the environment. For example, object recognition may be used to detect particular objects such as a baby monitor, construction machinery, or door, while facial recognition may be used to detect the face of a particular person in the vicinity of the user.

In some implementations, the sensor processing engine 390 includes one or more ML models for performing object and/or facial recognition. For example, the sensor processing engine 390 may include an ML model for recognizing objects. The model for recognizing objects may receive image data (e.g., videos and/or images) as an input and parse the data to identify recognizable objects. For example, the ML model may receive an image of the environment behind the user and identify a truck in the image. The identified object(s) may then be provided as an output of the ML model. In another example, the sensor processing engine 390 may include an ML model for recognizing people which may receive an image from the user's environment and by accessing a data store containing images of identified faces, may identify one or more people in the image. The data store containing images of identified faces may be stored in the memory 330. Additionally or alternatively, the data store containing images of identified faces may be stored in a cloud storage medium and may be accessed via a network. Images of identified faces may be user-specific such that people who are associated with the user can be identified when needed. In this manner, in determining whether a sound source that is a person should be visualized, the system 300 can take into whether the person is associated with the user (e.g., the user's manager may need to be visualized while an unknown passerby may not need to be visualized).

The recognized object(s) and/or faces may be transmitted to the source recognition engine 340 to assist in identifying sound sources for the audio signals received via the microphones 310. For example, information about the recognized objects and/or faces may be compared with the parameters of the received audio signals to determine if the parameters correspond with any of the recognized objects and/or faces.

The identified parameters of the sound signals, the captured sensor signals, the identified sound source and/or the recognized objects and faces may be transmitted to a source localization engine 355 to assist in identifying the location of each identified sound source. In some implementations, localization of the sound source is achieved by performing sound triangulation or sound trilateration. In alternative implementations, the location of the sound is determined by using sensor signals such as images and/or videos. In other examples, both sound and sensor signal analyses are performed to localize the sound source efficiently and accurately. When performing sound localization, in addition to determining the location of the sound source, the positional direction of the sound source with respect to the user may also be calculated. This may be done to determine whether the sound source is within or outside the field of the view of the user and may involve determining which direction the user is facing and how that direction corresponds with the location of the sound source. For example, after it is determined that the sound source is at a specific x, y and/or z coordinate, it may be determined how those coordinates correspond with the location of the user and/or the way the user is facing. This may need to occur in implementations where the microphones and/or the cameras are located at different locations than the user. Furthermore, the distance of the sound source from the user may be calculated. The distance may be used to determine the level of importance and/or danger of the sound source and as such may be used in determining whether the sound source should be visualized.

In some implementation, sensor signal may be used to also calculate the speed of a moving sound source with respect to the user. This may be performed for objects that are moving at specific rates with respect to the user and may take into account both the speed and direction of travel of the sound source and the user, when the user is also moving. For example, when the user is walking forward while a vehicle is driving towards the user from behind, the speed and direction of both the user and the vehicle may be taken into account to calculate the speed of the vehicle with respect to the user. Thus, the source localization engine 355 may determine the location, positional direction, speed and/or distance of one or more identified sound sources with respect to the user.

The location information of the one or more sound sources may be transmitted by the source localization engine 355 to an important source identification engine 345. The important source identification engine 345 may receive the location, positional direction and/or distance information along with one or more parameters of the audio signal and/or sensor signals to determine whether the identified sound sources qualify as important sound sources for visualization. This may first involve determining whether an identified source falls outside the field of view of the user. This is because, the user is likely aware of the sources that fall within the user's field of view and as such those sources may not need to be visualized. The process of determining whether a source falls outside the user's field of view may involve examining the location, positional direction and/or distance of the source from the user.

Once it is determined that a sound source falls outside the user's field of view, the process may proceed to determine whether the identified sound source qualifies as a source that should be visualized. This may involve taking into account parameters such as sound intensity (e.g., loudness), distance from the user, importance of the sound source to the user and others in determining whether the sound source should be visualized. For example, the important source identification engine 345 may analyze the sound intensity to determine if the loudness of the audio signal indicates that it is important and/or urgent. For example, the loudness of the sound of a person speaking behind the user may indicate that the person is trying to get the user's attention and/or that the conversation is important. The distance may also indicate urgency and/or importance of the sound. For example, an alert sound from a construction vehicle that is 50 feet away may be less important than an alert sound from a construction vehicle that is 20 feet away. In some implementations, the speed with which the sound source is approaching the user may also be taken into account for safety purposes.

Furthermore, the identified sound source may be analyzed to determine importance of the sound source. That is because certain sound sources may be more important for safety reasons. Other sound sources may be important to specific users. For example, the sound of the user's manager may be important to a specific user. This information may be taken into account by examining a user-specific data set. In some implementations, the user may be able to customize the data set by identifying sound sources that are important to the user. For example, the user may be able to utilize a user interface element of a computing device associated with or in communications with the system 300 to select sound sources that are important to the user.

In some implementations, the important source identification engine 345 may include one or more ML models for identifying important sound sources. By analyzing information about the audio signals, sensor signals, user-specific data, identified sound sources and/or location data, the important source identification engine 345 may determine whether an identified sound source qualifies as an important source for visualization.

Once it is determined that an identified sound source qualifies as an important source, information about the identified sound source may be transmitted to the source visualization engine 365 for visualizing the sound source. The transmitted information may include the identified sound source, the level of sound intensity (e.g., loudness), the distance of the sound source from the user, positional direction of the sound source with respect to the user, the speed and/or direction of movement of the sound source with respect to the user, and/or whether the user is stationary or moving. The collected information may be analyzed to display a visual representation of the sound source on a display system 370. The display system 370 may include one or more display panels and other elements that can generate a digital display on display panels. The display system 370 may receive instructions from the processor 350 that direct when and if certain visual representations need to be moved or modified to enhance the user's experience.

The processor 350 may include one or more processors for executing computer readable instructions stored in memory 330 in order to perform processes discussed herein. Additionally, the processor 350 may include one or more hardware or firmware logic units configured to execute hardware or firmware instructions. The processor 350 may be single-core or multicore, and the programs executed thereon may be configured for parallel or distributed processing. The processor 350 may optionally include individual components that are distributed throughout two or more devices, which may be remotely located and/or configured for coordinated processing. One or more aspects of the processor 350 may be virtualized and executed by remotely accessible networked computing devices configured in a cloud computing configuration. Furthermore, the processor 350 may make use of computing platforms based on DSP/FPGA (Digital Signal Processing/Field Programmable Gate Array) systems, and the like, which may not have an operating system. Although shown as separate units, in at least one implementation, each of the sensor processing engine 390, audio processing engine 320, source recognition engine 340, source localization engine 355, important source identification engine 345 and/or source visualization engine 365 are integrated with one or more elements of the processor 350.

The memory 330 may be in communication with the processor 350, audio processing engine 320, source recognition engine 340 and/or sensor processing engine 390. The communication may be wired or wireless and it may be direct or through one or more additional devices. Memory 330 may include removable media and/or built-in devices. For example, memory 330 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Memory 330 may also include devices with one or more of the following characteristics: volatile, non-volatile, dynamic, static, read/write, read-only, random access, sequential access, location addressable, file addressable, and content addressable.

In some implementations, the sensor processing engine 390, audio processing engine 320, source recognition engine 340, source localization engine 355, important source identification engine 345, source visualization engine 365, and/or the processor 350 may be integrated into one or more common devices, such as an application specific integrated circuit or a system on a chip. Furthermore, memory 330 may be a part of a storage device that is accessed remotely, through wired or wireless communication. For example, memory 330 take form of a cloud computing configuration. The internal hardware structure of the system 300 is discussed in greater detail in regard to FIGS. 6 and 7.

Figure 4A:
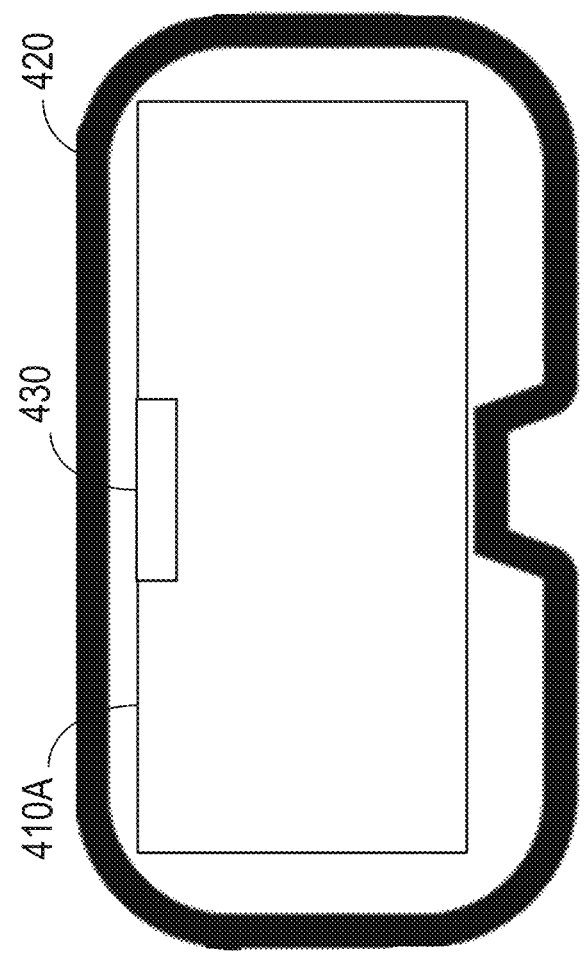
FIGS. 4A-4D depict example user interface screens on a display panel of a head-mounted display device for visualizing sound sources that are located outside the user's field of view.

FIGS. 4A-4D depict example user interface (UI) screens on a display panel of an HMD device for visualizing sound sources that are located outside the user's field of view. FIG. 4A depicts a UI screen 410A on a display panel 420 of an HMD 400. The UI screen 410 may function as a virtual surface which, while being displayed on the display panel 420, may appear to the user be further away from the user to create an appearance of a virtual or immersive environment. In some implementations, the UI screen 410A may include an expandable UI element 430 for displaying visual representations of sound sources that are outside the user's field of view. The UI element 430 may functions as a UI button which is displayed on the middle upper edge of the UI screen 410 and which can be expanded, when needed. When not use (e.g., where there is no need for visualizing a sound source), the UI element 430 may be minimized, as depicted in the UI screen 410A to reduce interference with the user's view of the environment.

Figure 4B:
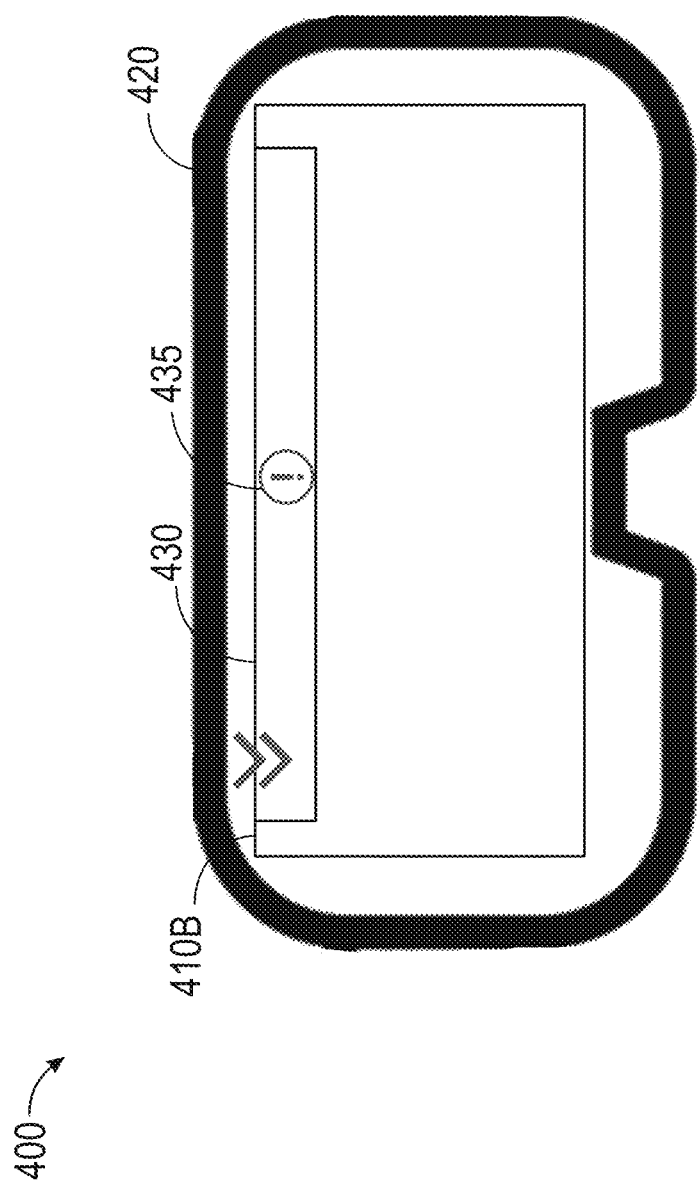
Figure 4C:
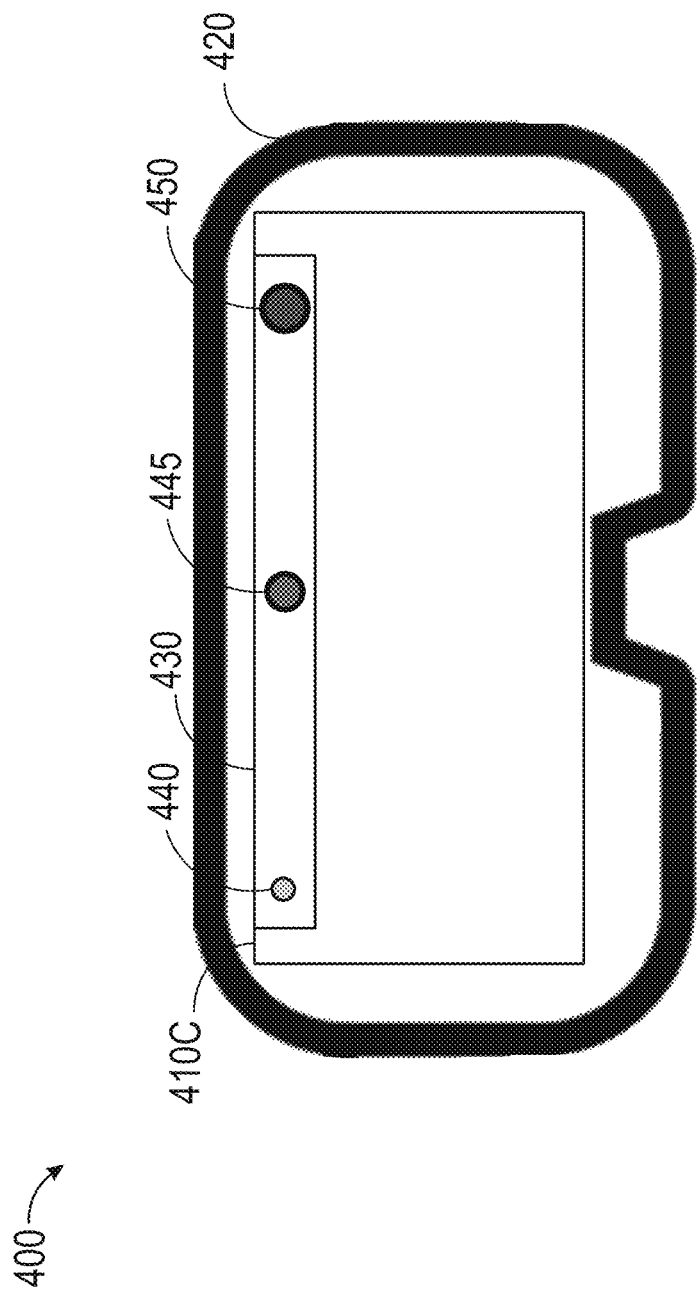

Once a need for visualizing a sound source arises, the UI element 430 may be expanded, as illustrated in the UI screen 410B of FIG. 4B. This may occur automatically, once an important sound source that is located outside the user's field of view is identified. For example, when the HMD 400 identifies a sound that indicates a construction vehicle is approaching the user from behind, the UI element 430 may automatically expand to its full size as depicted in the UI screen 410B. In some implementations, upon expansion, a virtual object such as a caution icon 435 may be displayed in the UI element 430 to bring the user's attention to the UI element 430. The caution icon 435 may be a flashing icon and/or may include other characteristics that attract the user's attention.

Once the UI element 430 has been expanded and the user's attention has been attracted, a visual representation of the identified sound source may be displayed in the UI element 430. This is depicted in the UI screen 410C of FIG. 4C which includes display elements 440, 445, 450. In some implementations, each of the display elements 440, 445, 450 represent the same sound source, but they each have different sound intensities and/or are located at different distances from the user. In some implementations, the size and/or color of the display element displayed may signify the loudness of the sound and/or closeness of the sound source. For example, a smaller-sized display element such as display element 440 may indicate that the sound is not very loud, while a medium-sized display element such as the display element 445 may demonstrate that the sound has medium loudness. A large-sized display element such as display element 450, on the other hand, may indicate that the identified sound is relatively loud. Similarly, a light color may indicate that the identified sound is not very loud, while a darker color may represent a louder sound. Different color schemes may be used in different configurations. For example, light colors may be used for high volume and dark colors for low volume. In some implementations, the color and/or size of the display element progressively change as the volume of the sound changes to indicate loudness of the sound.

In some implementations, the color of the display element may correspond with loudness, while the size of the display element corresponds with the distance from the user, or vice versa. For example, the large size of the display element 450 may indicate that the sound source is very close to the user, while its dark color indicates that the volume of the sound generated by the sound source is high. However, a large display element 450 having a light color may indicate that while the sound source is close to the user, it has a low volume.

In alternative implementations, the color and/or size of the display element may be used to indicate loudness of the sound, while the location at which the display element is displayed within the UI element 430 may correspond with the distance of the sound source from the user. In some implementations, the left edge of the UI element 430 represents the farthest point from the user, while the right edge represents the closest distance to the user. Thus, the element 440 displayed on the left side of the UI element 430 may indicate that the sound source is far from the user, while the display element 450 indicates that the sound source is very close to the user. In some implementations, for a moving sound source (e.g., if the sound source is getting closer to the user), the display element may be shown as moving in the UI element 430 (e.g., moving from the left side to the right side). In this manner, the user can be quickly notified of a sound source and its distance and/or intensity of the sound, as well as whether or not the sound source is getting closer or further from the user.

In some implementations, the display elements displayed within the UI element 430 correspond with the identified sound source. For example, the display elements may be visual representations of the sound source (e.g., holographic and/or other types of icons that represent the sound source). In an example, if the sound source is identified as a person, a human icon is shown. If the identity of the person is known, more information about the person may be presented along with the icon (e.g., a picture of their face and/or their name). In another example, if the sound source is identified as a conversation, a conversation icon is displayed. In yet another example, display elements that indicate imminent danger are used to provide prompt notification of danger. In some implementations, if important sound sources are identified for which the identity of the sound source has not been determined, a specific display element may be used to indicate that the sound source is unknown.

Figure 4D:
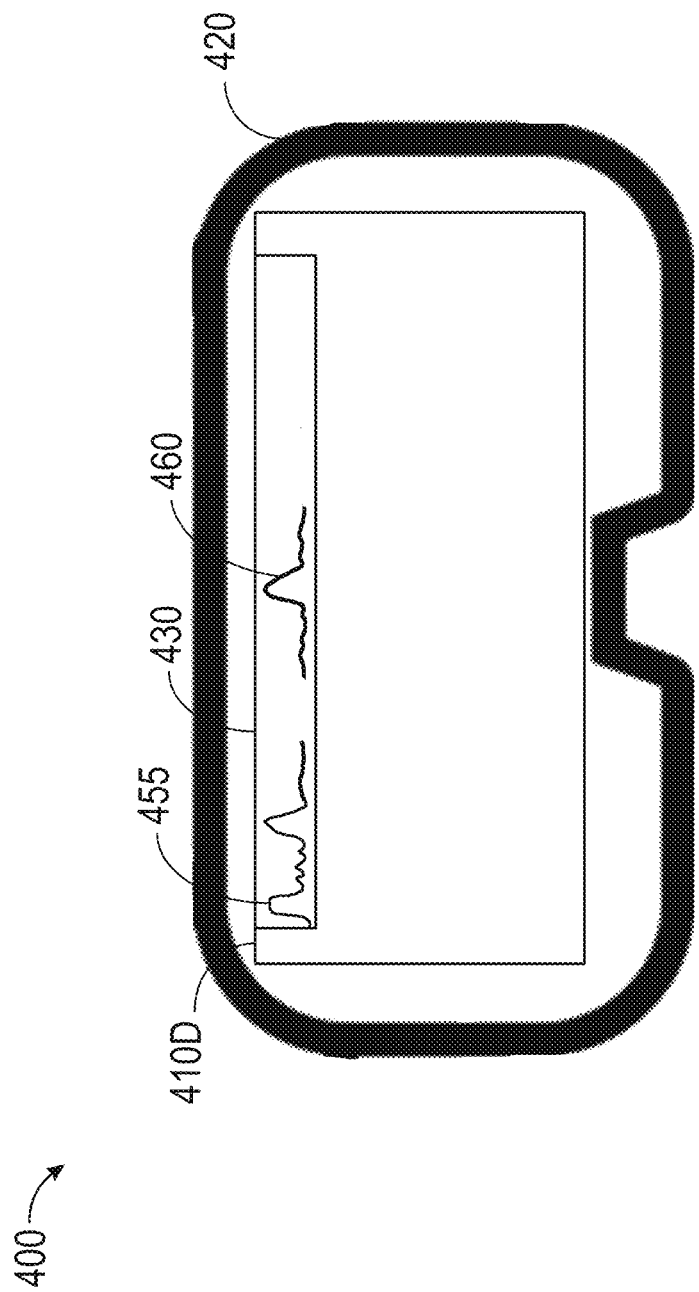

UI screen 410D of FIG. 4D depicts an alternative display element 455 for visualizing an important sound source. The display element 455 may be a sinewave, which in at least in some implementations, corresponds to the intensity of the source audio signal for a sound source that has been identified as an important sound source. For example, if a crying child that is located behind the user is identified as an important sound source, the sinewave display element 455 may be used to represent the sound source, while the curvature of the sinewave corresponds to the intensity of the audio signal generated by the crying child. In some implementations, the location at which the sinewave display element is displayed may provide an indication for the location of the sound source. For example, the display element 455 which is located at the left side of the UI element 430 may indicate that the sound source is located on the left side behind the user, while the display element 460 may indicate that the sound source is located right behind the user. Thus, in some implementations, the left, center and right side of the UI element may be used to display representations for sound sources that are located behind the user on the left, center and right sides. Thus, the UI element 430 may function as a rearview display (e.g., a rearview reflector) for providing visual representations of sound sources that are located behind the user. In an example, if the user begins moving while the UI element 430 is displaying a display element, the location, of the display element may change to indicate the changing direction of the sound source with respect to the user color. If the user moves far enough away from the sound source, the visual representation of the sound source may be removed from the UI element 430. In another example, if the user turns his/her head such that the sound source is no longer outside his/her field of view (e.g., the user can now see the sound source), the visual representation may also be removed. Furthermore, if the intensity and/or distance of the sound source with respect to the user changes as a result of user movement and/or the sound source movement, the color and/or size of the display element may be modified to illustrate the change.

In some implementations, sounds originating from within the person's field of view are also be visualized. In an example, sounds originating from the person's peripheral field of view are visualized. In another example, the user may select (e.g., via a UI interface) the types of sounds that the user desires to be visualized (e.g., outside the field of view, within the field of view, and/or within the peripheral point of view).

Figure 5:
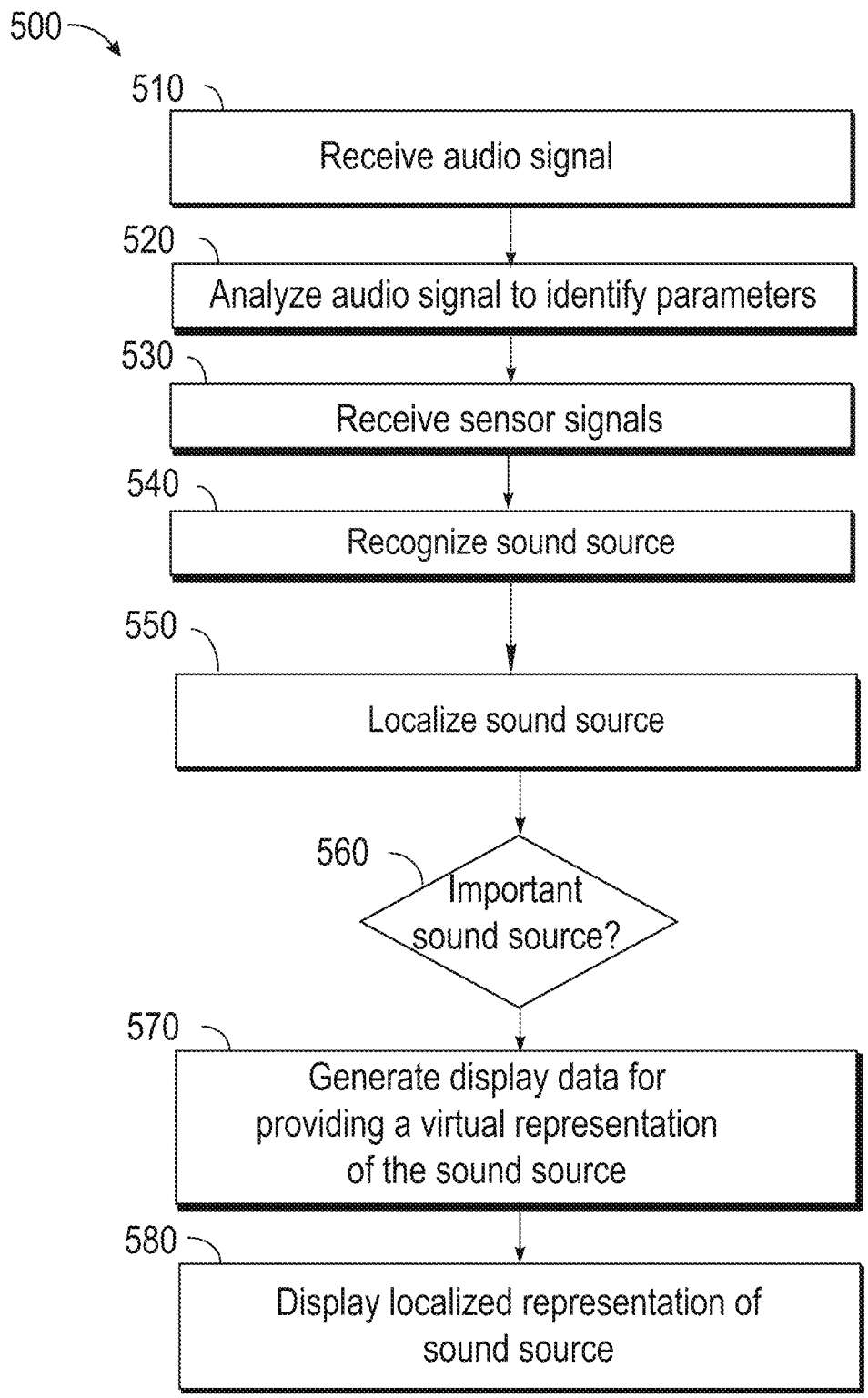
FIG. 5 is a flow diagram depicting an example method for identifying, localizing and visualizing important sound sources.

FIG. 5 is a flow diagram depicting an example method 500 for identifying, localizing and visualizing important sound sources. In some implementations, the steps of method 500 may be performed by a system such as the system 300 of FIG. 3. At 510, method 500 may begin receiving audio sounds from the ambient environment. Audio sounds may include any audio signal that is generated in the real-world in the vicinity of the system 300 and/or in the vicinity of the user. In one implementation, the audio sounds are received and captured by one or more microphones such as the microphones 310 of FIG. 3. This means that, in at least in one implementation, the method 500 is constantly listening to the ambient environment and receiving audio signals when and if there is a sound. In another implementation, the system may not be constantly listening. Instead, it may periodically wake up to listen for changes or may simply just listen to see if there is a significant change. This can be used particularly for environments in which sounds do not change very often. In such a system, historical information may be used to determine noise level, echo level, and the like, instead of performing a complete sound decomposition of the entire field continuously. For example, if the user is in a coffee shop, there is background noise that changes but not too much. In such an environment, the system may use historical information to measure the sound field instead of performing a complete sound decomposition. This may include recording the audio signals received to enable the system to perform historical analysis.

Once an audio signal (e.g., non-background noise audio signal) is received, method 500 may proceed to analyze the received audio signal to identify certain parameters for the signal, at 520. In one implementation, these parameters include at least one of intensity (volume), frequency, bandwidth, resolution, noise level, and echo level.

At 530, method 500 may include receiving one or more sensor signals form sensors configured to capture and/or measure one or more parameters of the real-world environment surrounding the user. For example, the sensor signals may include images, videos, motion information and accelerometer data about the user and/or one or more objects or people within the user's vicinity. This information may assist the method 500 examine the user's environment, identify sound sources and/or determine distances and orientation of the sound sources from the user, among other features. This may be done by analyzing the received sensor signals to identify certain parameters, characteristics, and/or objects in the environment. For example, facial recognition and object recognition algorithms may be used to identify certain people and/or objects, as discussed in detail with respect to FIG. 3. It should be noted that although receiving sensor signals is displayed as being performed after receiving audio signals, in other implementations, the sensor signals may be received and analyzed before or during the time period when audio signals are received and analyzed.

The analyzed sensor signals and/or audio signal parameters may be used, at 540, to identify a source for the audio signal, as discussed above with respect to FIG. 3. Once a source has been identified or it is determined that the sound source is unrecognizable, method 500 may proceed to localize the sound source, at 550. This may be achieved by examining the audio signal parameters and/or sensor signals to determine a location for the sound source. In some implementations, in addition to location, the positional direction of the sound source with respect to the user may also be calculated. This may be done to determine whether the sound source is within or outside the field of the view of the user and may involve determining which direction the user is facing and how that direction corresponds with the location of the sound source. Furthermore, the process of localizing the sound source may include determining the speed and directional change of the sound source with respect to the user in instances when the user and/or the sound source are moving.

Once the location information of the sound source has been determined, method 500 may proceed to determine if the sound source qualifies as an important sound source, at 560. This may involve examining the sound parameters, sensor parameters, location information and/or identity of the sound source if identified, to determine if the sound source is one that qualifies as an important sound source. Important sound source may include sound sources that are likely to be relevant to the user and/or relate to safety.

Additionally, in determining whether a sound source qualifies as an important sound source, method 500 may take into account whether the sound source falls outside the user's field of view. Sound sources that fall within the user's field of view may be considered unimportant since the user is likely to be already aware of those sound sources even if the user cannot hear them.

When it is determined that the sound source is an important sound source (560, yes), method 500 may proceed to generate display data for providing a visual representation of the sound source on a virtual surface, at 570. The generated display data may then be utilized to display a localized representation of the sound source, at 580. In some implementations, the location of the visual representation corresponds to a reflector location of the sound source, such that a rearview display element is provided.

Thus, in different implementations, a technical solution is provided for an improved method and system of identifying, localizing and visualization sound sources that fall outside the user's field of view. The technical solution provides a mechanism for efficiently identifying important an sound source, localizing the sound source and providing a visual representation that corresponds with the location of the sound source. Thus, the technical solution provides a mechanism for identifying sound sources that are likely to be important to the user and/or outside the user's field of view and providing a representation of such sound sources in a user-friendly manner that quickly and efficiently notifies the user of significant events such as imminent danger.

Figure 6:
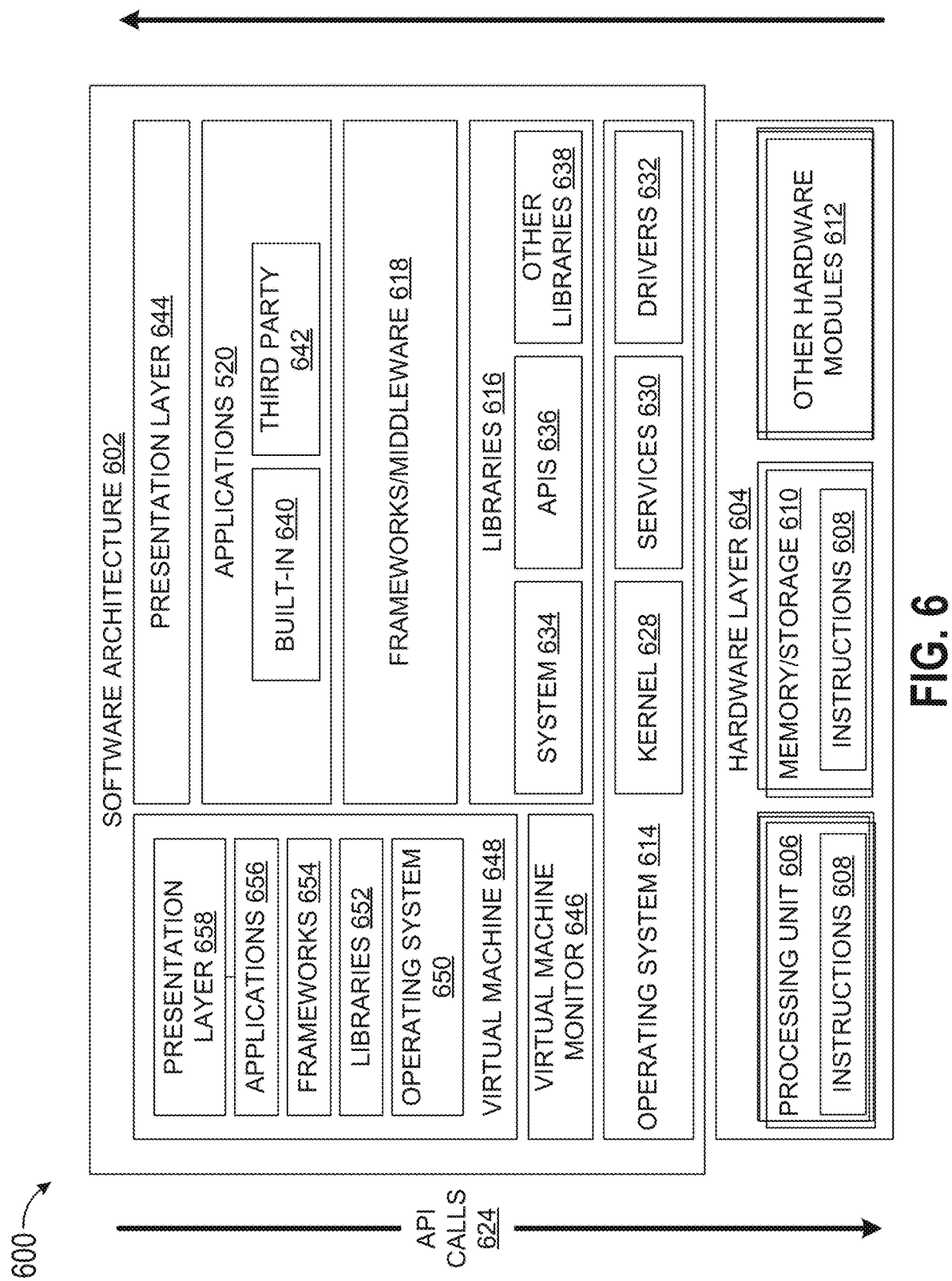
FIG. 6 is a block diagram illustrating an example software architecture, various portions of which may be used in conjunction with various hardware architectures herein described.

FIG. 6 is a block diagram 600 illustrating an example software architecture 602, various portions of which may be used in conjunction with various hardware architectures herein described, which may implement any of the above-described features. FIG. 6 is a non-limiting example of a software architecture and it will be appreciated that many other architectures may be implemented to facilitate the functionality described herein. The software architecture 602 may execute on hardware such as client devices, native application provider, web servers, server clusters, external services, and other servers. A representative hardware layer 604 includes a processing unit 606 and associated executable instructions 608. The executable instructions 608 represent executable instructions of the software architecture 602, including implementation of the methods, modules and so forth described herein.

The hardware layer 604 also includes a memory/storage 610, which also includes the executable instructions 608 and accompanying data. The hardware layer 604 may also include other hardware modules 612. Instructions 608 held by processing unit 608 may be portions of instructions 608 held by the memory/storage 610.

The example software architecture 602 may be conceptualized as layers, each providing various functionality. For example, the software architecture 602 may include layers and components such as an operating system (OS) 614, libraries 616, frameworks 618, applications 620, and a presentation layer 624. Operationally, the applications 620 and/or other components within the layers may invoke API calls 624 to other layers and receive corresponding results 626. The layers illustrated are representative in nature and other software architectures may include additional or different layers. For example, some mobile or special purpose operating systems may not provide the frameworks/middleware 618.

The OS 614 may manage hardware resources and provide common services. The OS 614 may include, for example, a kernel 628, services 630, and drivers 632. The kernel 628 may act as an abstraction layer between the hardware layer 604 and other software layers. For example, the kernel 628 may be responsible for memory management, processor management (for example, scheduling), component management, networking, security settings, and so on. The services 630 may provide other common services for the other software layers. The drivers 632 may be responsible for controlling or interfacing with the underlying hardware layer 604. For instance, the drivers 632 may include display drivers, camera drivers, memory/storage drivers, peripheral device drivers (for example, via Universal Serial Bus (USB)), network and/or wireless communication drivers, audio drivers, and so forth depending on the hardware and/or software configuration.

The libraries 616 may provide a common infrastructure that may be used by the applications 620 and/or other components and/or layers. The libraries 616 typically provide functionality for use by other software modules to perform tasks, rather than rather than interacting directly with the OS 614. The libraries 616 may include system libraries 634 (for example, C standard library) that may provide functions such as memory allocation, string manipulation, file operations. In addition, the libraries 616 may include API libraries 636 such as media libraries (for example, supporting presentation and manipulation of image, sound, and/or video data formats), graphics libraries (for example, an OpenGL library for rendering 2D and 3D graphics on a display), database libraries (for example, SQLite or other relational database functions), and web libraries (for example, WebKit that may provide web browsing functionality). The libraries 616 may also include a wide variety of other libraries 638 to provide many functions for applications 620 and other software modules.

The frameworks 618 (also sometimes referred to as middleware) provide a higher-level common infrastructure that may be used by the applications 620 and/or other software modules. For example, the frameworks 618 may provide various graphic user interface (GUI) functions, high-level resource management, or high-level location services. The frameworks 618 may provide a broad spectrum of other APIs for applications 620 and/or other software modules.

The applications 620 include built-in applications 620 and/or third-party applications 622. Examples of built-in applications 620 may include, but are not limited to, a contacts application, a browser application, a location application, a media application, a messaging application, and/or a game application. Third-party applications 622 may include any applications developed by an entity other than the vendor of the particular system. The applications 620 may use functions available via OS 614, libraries 616, frameworks 618, and presentation layer 624 to create user interfaces to interact with users.

Some software architectures use virtual machines, as illustrated by a virtual machine 628. The virtual machine 628 provides an execution environment where applications/modules can execute as if they were executing on a hardware machine (such as the machine 600 of FIG. 6, for example). The virtual machine 628 may be hosted by a host OS (for example, OS 614) or hypervisor, and may have a virtual machine monitor 626 which manages operation of the virtual machine 628 and interoperation with the host operating system. A software architecture, which may be different from software architecture 602 outside of the virtual machine, executes within the virtual machine 628 such as an OS 650, libraries 652, frameworks 654, applications 656, and/or a presentation layer 658.

Figure 7:
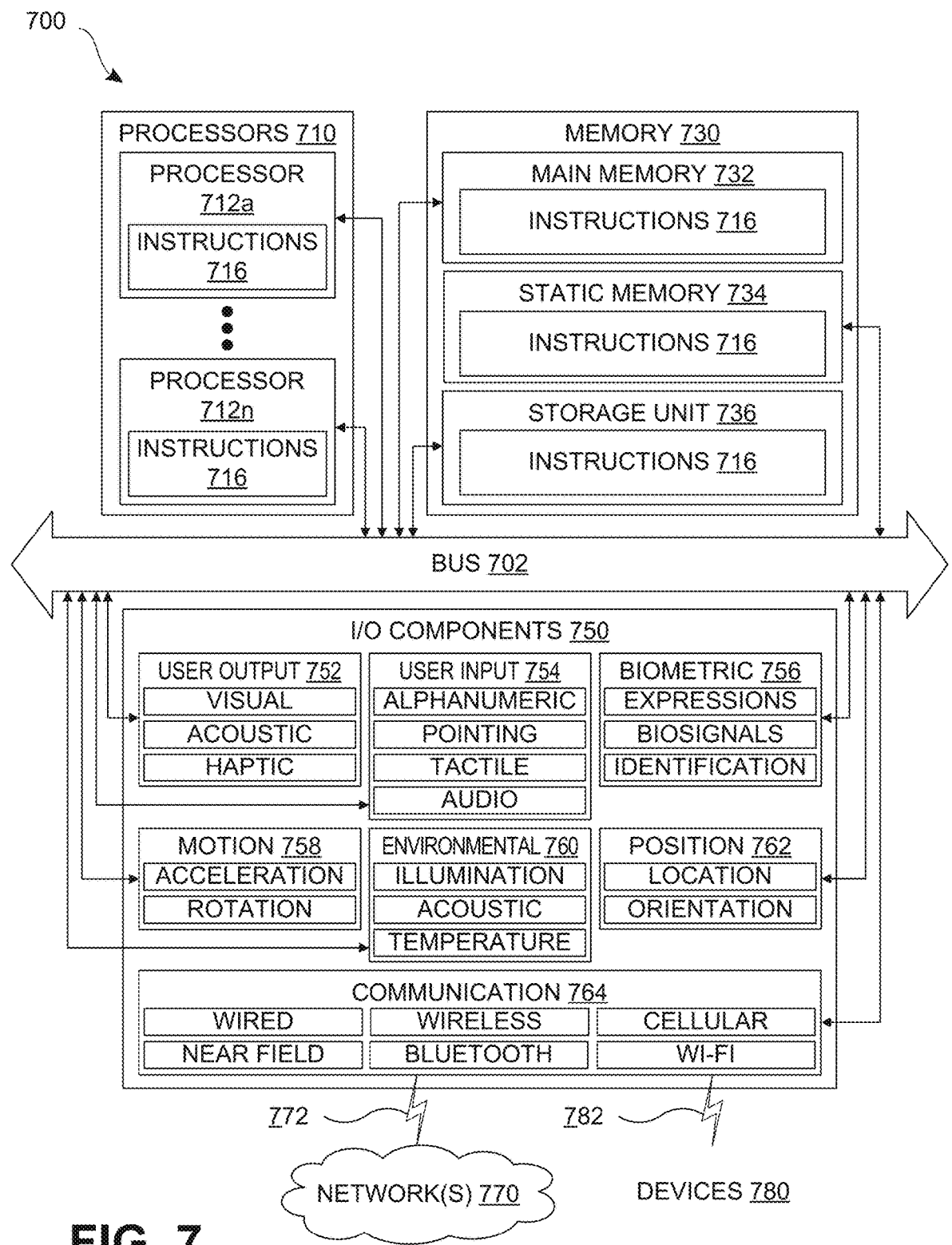
FIG. 7 is a block diagram illustrating components of an example machine configured to read instructions from a machine-readable medium and perform any of the features described herein.

FIG. 7 is a block diagram illustrating components of an example machine 700 configured to read instructions from a machine-readable medium (for example, a machine-readable storage medium) and perform any of the features described herein. The example machine 700 is in a form of a computer system, within which instructions 716 (for example, in the form of software components) for causing the machine 700 to perform any of the features described herein may be executed. As such, the instructions 716 may be used to implement methods or components described herein. The instructions 716 cause unprogrammed and/or unconfigured machine 700 to operate as a particular machine configured to carry out the described features. The machine 700 may be configured to operate as a standalone device or may be coupled (for example, networked) to other machines. In a networked deployment, the machine 700 may operate in the capacity of a server machine or a client machine in a server-client network environment, or as a node in a peer-to-peer or distributed network environment. Machine 700 may be embodied as, for example, a server computer, a client computer, a personal computer (PC), a tablet computer, a laptop computer, a netbook, a set-top box (STB), a gaming and/or entertainment system, a smart phone, a mobile device, a wearable device (for example, a smart watch), and an Internet of Things (IoT) device. Further, although only a single machine 700 is illustrated, the term "machine" includes a collection of machines that individually or jointly execute the instructions 716.

The machine 700 may include processors 710, memory 730, and I/O components 750, which may be communicatively coupled via, for example, a bus 702. The bus 702 may include multiple buses coupling various elements of machine 700 via various bus technologies and protocols. In an example, the processors 710 (including, for example, a central processing unit (CPU), a graphics processing unit (GPU), a digital signal processor (DSP), an ASIC, or a suitable combination thereof) may include one or more processors 712a to 712n that may execute the instructions 716 and process data. In some examples, one or more processors 710 may execute instructions provided or identified by one or more other processors 710. The term "processor" includes a multi-core processor including cores that may execute instructions contemporaneously. Although FIG. 7 shows multiple processors, the machine 700 may include a single processor with a single core, a single processor with multiple cores (for example, a multi-core processor), multiple processors each with a single core, multiple processors each with multiple cores, or any combination thereof. In some examples, the machine 700 may include multiple processors distributed among multiple machines.

The memory/storage 730 may include a main memory 732, a static memory 734, or other memory, and a storage unit 736, both accessible to the processors 710 such as via the bus 702. The storage unit 736 and memory 732, 734 store instructions 716 embodying any one or more of the functions described herein. The memory/storage 730 may also store temporary, intermediate, and/or long-term data for processors 710. The instructions 716 may also reside, completely or partially, within the memory 732, 734, within the storage unit 736, within at least one of the processors 710 (for example, within a command buffer or cache memory), within memory at least one of I/O components 750, or any suitable combination thereof, during execution thereof.

Accordingly, the memory 732, 734, the storage unit 736, memory in processors 710, and memory in I/O components 750 are examples of machine-readable media.

As used herein, "machine-readable medium" refers to a device able to temporarily or permanently store instructions and data that cause machine 700 to operate in a specific fashion. The term "machine-readable medium," as used herein, does not encompass transitory electrical or electromagnetic signals per se (such as on a carrier wave propagating through a medium); the term "machine-readable medium" may therefore be considered tangible and non-transitory. Non-limiting examples of a non-transitory, tangible machine-readable medium may include, but are not limited to, nonvolatile memory (such as flash memory or read-only memory (ROM)), volatile memory (such as a static random-access memory (RAM) or a dynamic RAM), buffer memory, cache memory, optical storage media, magnetic storage media and devices, network-accessible or cloud storage, other types of storage, and/or any suitable combination thereof. The term "machine-readable medium" applies to a single medium, or combination of multiple media, used to store instructions (for example, instructions 716) for execution by a machine 700 such that the instructions, when executed by one or more processors 710 of the machine 700, cause the machine 700 to perform and one or more of the features described herein. Accordingly, a "machine-readable medium" may refer to a single storage device, as well as "cloud-based" storage systems or storage networks that include multiple storage apparatus or devices.

The I/O components 750 may include a wide variety of hardware components adapted to receive input, provide output, produce output, transmit information, exchange information, capture measurements, and so on. The specific I/O components 750 included in a particular machine will depend on the type and/or function of the machine. For example, mobile devices such as mobile phones may include a touch input device, whereas a headless server or IoT device may not include such a touch input device. The particular examples of I/O components illustrated in FIG. 7 are in no way limiting, and other types of components may be included in machine 700. The grouping of I/O components 750 are merely for simplifying this discussion, and the grouping is in no way limiting. In various examples, the I/O components 750 may include user output components 752 and user input components 754. User output components 752 may include, for example, display components for displaying information (for example, a liquid crystal display (LCD) or a projector), acoustic components (for example, speakers), haptic components (for example, a vibratory motor or force-feedback device), and/or other signal generators. User input components 754 may include, for example, alphanumeric input components (for example, a keyboard or a touch screen), pointing components (for example, a mouse device, a touchpad, or another pointing instrument), and/or tactile input components (for example, a physical button or a touch screen that provides location and/or force of touches or touch gestures) configured for receiving various user inputs, such as user commands and/or selections.

In some examples, the I/O components 750 may include biometric components 756 and/or position components 762, among a wide array of other environmental sensor components. The biometric components 756 may include, for example, components to detect body expressions (for example, facial expressions, vocal expressions, hand or body gestures, or eye tracking), measure biosignals (for example, heart rate or brain waves), and identify a person (for example, via voice-, retina-, and/or facial-based identification). The position components 762 may include, for example, location sensors (for example, a Global Position System (GPS) receiver), altitude sensors (for example, an air pressure sensor from which altitude may be derived), and/or orientation sensors (for example, magnetometers).

The I/O components 750 may include communication components 764, implementing a wide variety of technologies operable to couple the machine 700 to network(s) 770 and/or device(s) 780 via respective communicative couplings 772 and 782. The communication components 764 may include one or more network interface components or other suitable devices to interface with the network(s) 770. The communication components 764 may include, for example, components adapted to provide wired communication, wireless communication, cellular communication, Near Field Communication (NFC), Bluetooth communication, Wi-Fi, and/or communication via other modalities. The device(s) 780 may include other machines or various peripheral devices (for example, coupled via USB).

In some examples, the communication components 764 may detect identifiers or include components adapted to detect identifiers. For example, the communication components 664 may include Radio Frequency Identification (RFID) tag readers, NFC detectors, optical sensors (for example, one- or multi-dimensional bar codes, or other optical codes), and/or acoustic detectors (for example, microphones to identify tagged audio signals). In some examples, location information may be determined based on information from the communication components 762, such as, but not limited to, geo-location via Internet Protocol (IP) address, location via Wi-Fi, cellular, NFC, Bluetooth, or other wireless station identification and/or signal triangulation.

While various embodiments have been described, the description is intended to be exemplary, rather than limiting, and it is understood that many more embodiments and implementations are possible that are within the scope of the embodiments. For example, even though some embodiments disclosed herein discuss the sound as originating from outside the person's field of view, in some implementations, sounds originating from within the person's field of view may also be visualized. In an example, sounds originating from the person's peripheral field of view are visualized. In another example, the person (e.g., user) may select the types of sounds that should be visualized (e.g., outside the field of view, within the field of view, and/or within the peripheral point of view). Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

Generally, functions described herein (for example, the features illustrated in FIGS. 1-5) can be implemented using software, firmware, hardware (for example, fixed logic, finite state machines, and/or other circuits), or a combination of these implementations. In the case of a software implementation, program code performs specified tasks when executed on a processor (for example, a CPU or CPUs). The program code can be stored in one or more machine-readable memory devices. The features of the techniques described herein are system-independent, meaning that the techniques may be implemented on a variety of computing systems having a variety of processors. For example, implementations may include an entity (for example, software) that causes hardware to perform operations, e.g., processors functional blocks, and so on. For example, a hardware device may include a machine-readable medium that may be configured to maintain instructions that cause the hardware device, including an operating system executed thereon and associated hardware, to perform operations. Thus, the instructions may function to configure an operating system and associated hardware to perform the operations and thereby configure or otherwise adapt a hardware device to perform functions described above. The instructions may be provided by the machine-readable medium through a variety of different configurations to hardware elements that execute the instructions.

In the following, further features, characteristics and advantages of the invention will be described by means of items:

Item 1. An electronic device comprising:
 a sound transducer for receiving an audio signal;
 a display unit;
 a processing unit; and
 a memory readable by the processing unit and comprising instructions stored thereon to cause the processing unit to:
  analyze an audio signal received by the sound transducer to determine a positional direction of a source of the received audio signal;
  determine whether the positional direction of the source falls outside a field of view of a user of the electronic device; and
  in response to determining that the positional direction of the source falls outside the field of view of the user of the electronic device, render on the display unit a visual representation of the source,
  wherein the visual representation of the source is rendered on a virtual surface at a location within the field of view of the user, the location corresponding to at least one of a distance of the source from the user and a positional direction of the source with respect to the user.

Item 2. The electronic device of item 1, wherein the memory further includes instructions which when executed cause the processing unit to:
 identify the source of the received audio signal; and
 determine whether the identified source is one of a plurality of sources for which the visual representation of the source should be rendered on the display unit.

Item 3. The electronic device of items 1 or 2, wherein the memory further includes instructions which when executed cause the processing unit to:
 determine the distance from the source of the received audio signal to the user of the electronic device; and
 determine based at least on the distance whether the visual representation of the source should be rendered on the display unit.

Item 4. The electronic device of any one of the preceding items, wherein the memory further includes instructions which when executed cause the processing unit to:
 determine whether at least one of the distance or the positional direction with respect to the user has changed; and
 responsive to determining that the at least one of the distance or the positional direction with respect to the user has changed, changing the position of the visual representation on the virtual surface.

Item 5. The electronic device of item 4, wherein the memory further includes instructions which when executed cause the processing unit to:
 determine whether the changed distance falls outside a threshold distance; and
 responsive to determining that the changed distance falls outside the threshold distance, discontinue rendering the visual representation of the source.

Item 6. The electronic device of any one of the preceding items, wherein the visual representation of the source is rendered on a virtual surface at a reflector location corresponding to a location of the source.

Item 7. The electronic device of any one of the preceding items, wherein the virtual representation includes an indication of a loudness of the received audio signal.

Item 8. A method for visualizing a sound source comprising:
 analyzing an audio signal received by a sound transducer to determine a positional direction of the sound source;
 determining whether the positional direction of the sound source falls outside a field of view of a user; and
 in response to determining that the positional direction of the sound source falls outside the field of view of the user, rendering on a display unit a visual representation of the sound source;
 wherein the visual representation of the sound source is rendered on a virtual surface at a location within the field of view of the user, the location corresponding to at least one of a distance of the sound source from the user and a positional direction of the sound source with respect to the user.

Item 9. The method of item 8, further comprising:
 identifying the source of the received audio signal, and
 determining whether the identified sound source is one of a plurality of sources for which the visual representation of the sound source should be rendered on the display unit.

Item 10. The method of items 8 or 9, further comprising:
 determining the distance from the sound source to the user; and
 determining based at least on the distance whether the visual representation of the sound source should be rendered on the display unit.

Item 11. The method of any of items 8-10, further comprising:
 determining whether at least one of the distance or the positional direction with respect to the user has changed; and
 responsive to determining that the at least one of the distance or the positional direction with respect to the user has changed, changing the position of the visual representation on the virtual surface.

Item 12. The method of item 11, further comprising:
 determining whether the changed distance falls outside a threshold distance; and
 responsive to determining that the changed distance falls outside the threshold distance, discontinue rendering the visual representation of the source.

Item 13. The method of any of items 8-12, wherein the visual representation of the source is rendered on a virtual surface at a reflector location corresponding to a location of the source.

Item 14. The method of any of items 8-13, wherein the virtual representation includes an indication of a loudness of the received audio signal.

Item 15. A non-transitory computer readable medium on which are stored instructions that, when executed by an operating system, cause a programmable device to:
analyze an audio signal received by a sound transducer to determine a positional direction of a sound source of the received audio signal;
determine whether the positional direction of the sound source falls outside a field of view of a user; and
in response to determining that the positional direction of the sound source falls outside the field of view of the user, rend on a display unit a visual representation of the sound source;
wherein the visual representation of the source is rendered on a virtual surface at a location within the field of view of the user, the location corresponding to at least one of a distance of the source from the user and a positional direction of the source with respect to the user.

Item 16. The computer readable medium of item 15, wherein the instructions further cause the programmable device to:
identify the source of the received audio signal, and
determine whether the identified source is one of a plurality of sources for which the visual representation of the sound source should be rendered on the display unit.

Item 17. The computer readable medium of items 15 or 16, wherein the instructions further cause the programmable device to:
determining the distance from the sound source to the user; and
determining based at least on the distance whether the visual representation of the sound source should be rendered on the display unit.

Item 18. The computer readable medium of any of items 15-17, wherein the visual representation of the source is rendered on a virtual surface at a reflector location corresponding to a location of the source.

Item 19. The computer readable medium of any of items 15-18, wherein the virtual representation includes an indication of a loudness of the received audio signal.

Item 20. The computer readable medium of any of items 15-19, wherein the instructions further cause the programmable device to:
determine whether the changed distance falls outside a threshold distance; and
responsive to determining that the changed distance falls outside the threshold distance, discontinue rendering the visual representation of the source.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows, and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein.

Relational terms such as first and second and the like may be used solely to distinguish one entity or action from another without necessarily requiring or implying any actual such relationship or order between such entities or actions. The terms "comprises," "comprising," and any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

The Abstract of the Disclosure is provided to allow the reader to quickly identify the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that any claim requires more features than the claim expressly recites. Rather, as the following claims reflect, inventive subject matter lies in less than all features of a single disclosed example. Thus, the following claims are hereby incorporated into the Detailed Description, with each claim standing on its own as a separately claimed subject matter.

What is claimed is:

1. An electronic device comprising:
a sound transducer for receiving an audio signal;
a display unit;
a processing unit; and
a memory readable by the processing unit and comprising instructions stored thereon to cause the processing unit to:
analyze the audio signal received by the sound transducer to determine a positional direction of a source of the received audio signal;
determine whether the positional direction of the source falls outside a field of view of a user of the electronic device;
calculate a distance from the source of the received audio signal to the user of the electronic device;

in response to determining that the positional direction of the source falls outside the field of view of the user of the electronic device, determine based on the calculated distance that a visual representation of the source should be rendered on the display unit; and render on the display unit the visual representation of the source, wherein the visual representation of the source is rendered on a virtual surface at a location within the field of view of the user, the location corresponding to at least one of the distance of the source from the user and a positional direction of the source with respect to the user.

2. The electronic device of claim 1, wherein the memory further includes instructions which when executed cause the processing unit to:

identify the source of the received audio signal; and determine whether the identified source is one of a plurality of sources for which the visual representation of the source should be rendered on the display unit.

3. The electronic device of claim 1, wherein the memory further includes instructions which when executed cause the processing unit to:

determine whether at least one of the distance or the positional direction with respect to the user has changed; and responsive to determining that the at least one of the distance or the positional direction with respect to the user has changed, changing the location of the visual representation on the virtual surface.

4. The electronic device of claim 3, wherein the memory further includes instructions which when executed cause the processing unit to:

determine whether the changed distance falls outside a threshold distance; and responsive to determining that the changed distance falls outside the threshold distance, discontinue rendering the visual representation of the source.

5. The electronic device of claim 1, wherein the visual representation of the source is rendered on the virtual surface at a reflector location corresponding to a location of the source.

6. The electronic device of claim 1, wherein the virtual representation includes an indication of a loudness of the received audio signal.

7. A method for visualizing a sound source comprising:

analyzing an audio signal received by a sound transducer to determine a positional direction of the sound source;

determining whether the positional direction of the sound source falls outside a field of view of a user;

calculating a distance from the sound source of the received audio signal to the user;

in response to determining that the positional direction of the sound source falls outside the field of view of the user, determining based on the calculated distance that a visual representation of the sound source should be rendered on a display unit; and rendering on the display unit the visual representation of the sound source;

wherein the visual representation of the sound source is rendered on a virtual surface at a location within the field of view of the user, the location corresponding to at least one of the distance of the sound source from the user and a positional direction of the sound source with respect to the user.

8. The method of claim 7, further comprising:

identifying the sound source of the received audio signal, and determining whether the identified sound source is one of a plurality of sources for which the visual representation of the sound source should be rendered on the display unit.

9. The method of claim 7, further comprising:

determining whether at least one of the distance or the positional direction with respect to the user has changed; and responsive to determining that the at least one of the distance or the positional direction with respect to the user has changed, changing the location of the visual representation on the virtual surface.

10. The method of claim 9, further comprising:

determining whether the changed distance falls outside a threshold distance; and responsive to determining that the changed distance falls outside the threshold distance, discontinue rendering the visual representation of the sound source.

11. The method of claim 7, wherein the visual representation of the sound source is rendered on the virtual surface at a reflector location corresponding to a location of the sound source.

12. The method of claim 7, wherein the virtual representation includes an indication of a loudness of the received audio signal.

13. A non-transitory computer readable medium on which are stored instructions that, when executed by an operating system, cause a programmable device to:

analyze an audio signal received by a sound transducer to determine a positional direction of a sound source of the received audio signal;

determine whether the positional direction of the sound source falls outside a field of view of a user;

calculate a distance from the sound source of the received audio signal to the user;

in response to determining that the positional direction of the sound source falls outside the field of view of the user, determine based on the calculated distance that a visual representation of the source should be rendered on a display unit; and render on the display unit the visual representation of the sound source;

wherein the visual representation of the sound source is rendered on a virtual surface at a location within the field of view of the user, the location corresponding to at least one of the distance of the sound source from the user and a positional direction of the sound source with respect to the user.

14. The computer readable medium of claim 13, wherein the instructions further cause the programmable device to:

identify the sound source of the received audio signal, and determine whether the identified sound source is one of a plurality of sources for which the visual representation of the sound source should be rendered on the display unit.

15. The computer readable medium of claim 13, wherein the visual representation of the sound source is rendered on a virtual surface at a reflector location corresponding to a location of the sound source.

16. The computer readable medium of claim 13, wherein the virtual representation includes an indication of a loudness of the received audio signal.

17. The computer readable medium of claim 13, wherein the instructions further cause the programmable device to:

determine whether at least one of the distance or the positional direction with respect to the user has changed;
determine whether the changed distance falls outside a threshold distance; and
responsive to determining that the changed distance falls outside the threshold distance, discontinue rendering the visual representation of the source.

* * * * *